(12) United States Patent
Khatchatrian et al.

(10) Patent No.: US 6,859,049 B2
(45) Date of Patent: Feb. 22, 2005

(54) DIAGNOSTIC COMPLEX FOR MEASUREMENT OF THE CONDITION OF BIOLOGICAL TISSUES AND LIQUIDS

(76) Inventors: Robert G. Khatchatrian, 809 E. Chestnut St., #8, Glendale, CA (US) 91205; Ashot P. Khatchatrian, 809 E. Chestnut St., #8, Glendale, CA (US) 91205; Asmik Aruntyunyan, 809 E. Chestnut St., #8, Glendale, CA (US) 91205

( * ) Notice: Subject to any disclaimer, the term of this patent is extended or adjusted under 35 U.S.C. 154(b) by 0 days.

(21) Appl. No.: 10/306,895

(22) Filed: Nov. 25, 2002

(65) Prior Publication Data

US 2003/0214312 A1 Nov. 20, 2003

Related U.S. Application Data

(63) Continuation of application No. 09/827,130, filed on Apr. 5, 2001, now abandoned, which is a continuation of application No. 08/879,523, filed on Jun. 20, 1997, now Pat. No. 5,987,353, which is a continuation-in-part of application No. 08/831,689, filed on Apr. 10, 1997, now abandoned.

(51) Int. Cl.[7] .......................... G01R 27/08; A61B 5/053
(52) U.S. Cl. ........................ 324/692; 324/693; 600/547
(58) Field of Search ................................ 324/692, 691, 324/693, 707; 600/547, 576, 373

(56) References Cited

U.S. PATENT DOCUMENTS

| | | | | |
|---|---|---|---|---|
| 3,674,012 A | * | 7/1972 | Sage | 600/369 |
| 3,851,641 A | * | 12/1974 | Toole et al. | 600/529 |
| 4,184,486 A | | 1/1980 | Papa | 600/373 |
| 5,282,840 A | | 2/1994 | Hudrlik | 607/28 |
| 5,630,426 A | | 5/1997 | Eggers et al. | 600/547 |
| 5,987,353 A | * | 11/1999 | Khatchatrian et al. | 600/547 |
| 6,184,688 B1 | * | 2/2001 | Kamitani | 324/519 |

* cited by examiner

Primary Examiner—Anjan K. Deb
(74) Attorney, Agent, or Firm—Knobbe, Martens, Olson & Bear, LLP

(57) ABSTRACT

Assembly kit for an apparatus and a method for simultaneously obtaining biological sample and measuring its electrical resistance at at least two different frequencies for diagnosis of sample condition. The apparatus includes a main case; an aspirating needle connected to main case for obtaining biological liquid sample; a liquid collector connected to aspirating needle for receiving biological liquid has a metal conductor in electrical contact with the needle and a metal piston; and an electro-impedance meter. The method includes the steps of contacting biological tissue with an electrically conductive hook having a pointed end as a first electrode and a second electrode; measuring electrical impedance of the biological tissue contacted with the first and second electrodes at at least two different frequencies; and excising a part of the biological tissue with the pointed end of the hook to obtain a sample of the biological tissue.

19 Claims, 6 Drawing Sheets

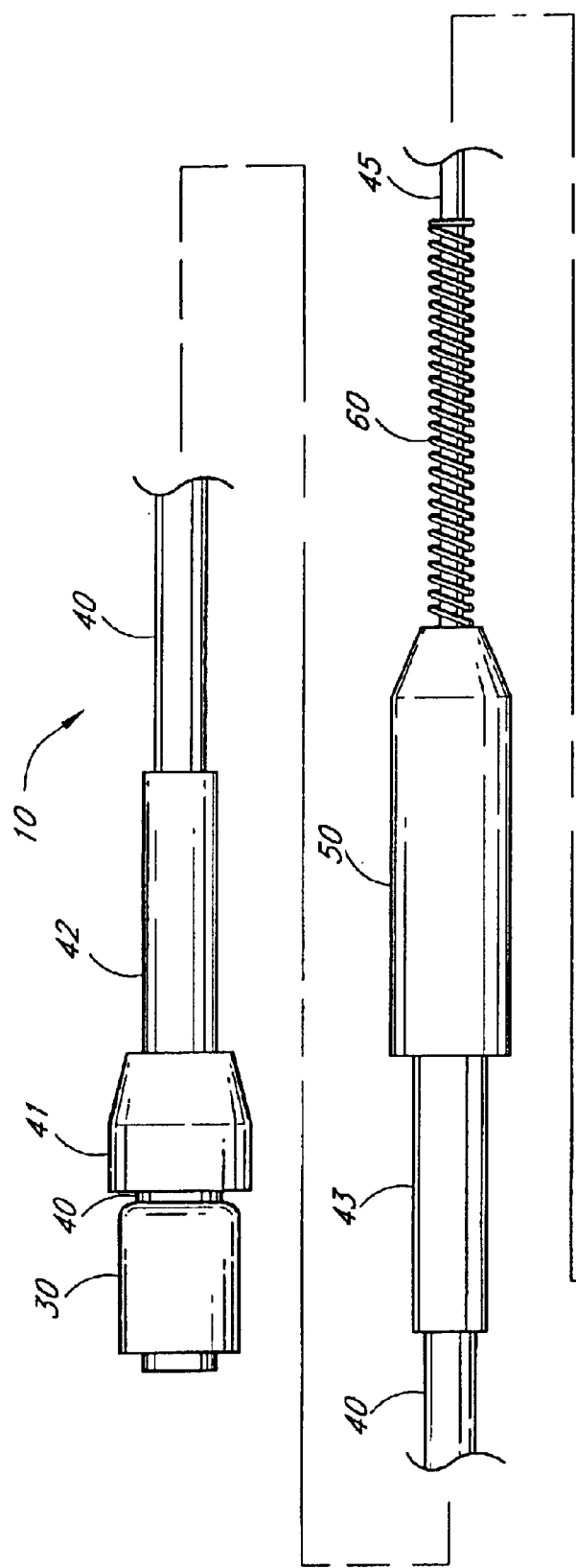
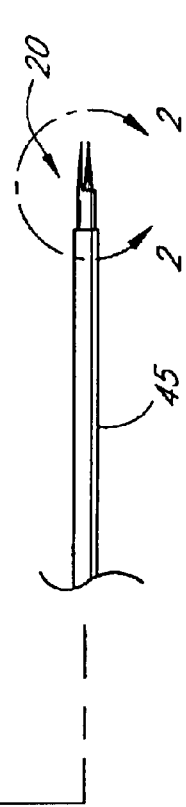
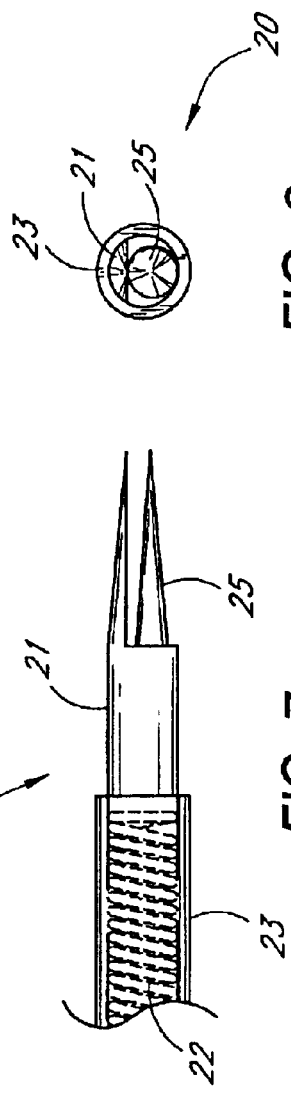
FIG. 6
FIG. 7
FIG. 8

DIAGNOSTIC COMPLEX FOR MEASUREMENT OF THE CONDITION OF BIOLOGICAL TISSUES AND LIQUIDS

RELATED APPLICATIONS

This application is a continuation of application Ser. No. 09/827,130 filed Apr. 5, 2001, now abandoned, which is a continuation of 08/897,523 filed Jun. 20, 1997, now U.S. Pat. No. 5,987,353, which is a continuation-in-part of application Ser. No. 08/831,689, filed Apr. 10, 1997, now abandoned.

FIELD OF THE INVENTION

The present invention relates to electroimpedance measurements of mammalian biological tissues and liquids with the use of an apparatus and method for simultaneously sampling a biological tissue or liquid and for measuring the complete electrical resistance of the biological tissue or liquid for the purpose of diagnosis of the condition of the tissue or liquid.

BACKGROUND OF THE INVENTION

Studies of the dielectrical properties of human tissue types have been made since the late 19th century. All cells and biological tissues conduct electric charge to some degree. The conduction of charge within a cell is known to be affected by a variety of intrinsic and extrinsic factors. The cell has maximal electric conductivity at resistance measurement frequencies equal to 10 kHz and above (B. N. Tarusov. Biological Physics. Higher School Press, 1968). The raising of electric conductivity occurs at the expense of a reduction in capacitance producing complex resistance. At low frequencies of resistance measurement the direct transfer of charge carriers is hindered by the determined structures of a tissue or sub-cell membranes. These structures play a key role in cell polarization phenomena. In contrast, measurements at high frequencies show no influences of polarization phenomena on conductivity.

Thus, it is known that an increase of frequency of a measuring current decreases the complex resistance of a biological tissue or liquid. This phenomenon, named as the dispersion of resistance, is a property of a live cell or tissue. The dispersion of resistance is explained by the presence of polarization phenomena in the biological object—tissue or liquid. At the deterioration of a functional condition of a biological object the ability to achieve polarization decreases. The death of a biological object excludes the dispersion of its resistance and, hence, the ability of the cell to achieve polarization.

Thus, polarization as a phenomenon bears information about the functional condition of a biological object. Therefore, it is possible to evaluate a condition of a biological tissue or liquid with the relation of resistance measured at low frequency to resistance measured at high frequency, that is, with a factor of dispersion.

Devices for definition of a condition of biological tissues and liquids are known which function by measurement of biological tissue and liquid electrical resistance. The methods of electrical impedanceometry, based on measurement of active and reactive elements of the impedance, are widely applied in medicine for diagnosis of pathology of the cardiovascular system, diseases of lungs, etc. However, with the help of present methods of impedanceometry it is possible to receive only general information on changes in organs of the body. Such information in the majority of cases does not reflect the underlying structural changes in tissues. Separate elements of impedance have only been studied, which although reveal the dependence of electrical resistance of tissues on their structure, do not, however, provide sharp diagnostic information. Additionally, in many technical areas, the reliability of data received as a result of measurements of the information is considerably reduced with a reduction in the time of measurement. A reduction in the reliability of resistance measurements is also known to occur with a reduction in the time of measurement.

The majority of known devices for research of a functional condition of biological tissues and liquids, enabling the investigation of electrical parameters of biological tissues and liquids, do not provide sufficient accuracy of measurement of a module of the complete electrical resistance. This is because of errors, caused by drift of the voltage of displacement of zero in the operating amplifier, the influence of "parasitic capacities" in the measuring circuit and non-equivalence of a factor of transformation of signals of detectors under the effect of temporal and climatic factors.

In a known device in European Patent Application 0050353 A1, the condition of tissue is evaluated on a degree of distinction between the modules of complete electrical resistance of the tissue, measured serially at low and high frequencies. However, with serial measurement of modules of complete electrical resistance at different frequencies, loss or "failure" of information occurs, leading to a doubtful final result, as the condition of a biological object at the small site of measurement does not remain constant in the interval between measurements at high and low frequencies.

A device for researching the gastroenteric tract is known, the purpose of which is increasing the accuracy in diagnosis of peptic ulcer (Certificate of U.S. Ser. No. 1514347). The device consists of a flexible probe with movable half-cylindrical tubes inside the probe case, on the ends of which are fixed metal electrodes, of which the calomel electrode is attached to a hand of the patient and joins to a pH-meter via a switch plug. The design of this device limits the opportunity of the researcher, as it does not permit one to conduct a sampling of histological and cytological material with simultaneous measurement of electrical resistance of the researched object. This device addresses a problem of measurement of the pH of the gastric juice and cannot be used for multifinctional research studies.

Thus, there is a need for an improved multifunctional apparatus and method for obtaining mammalian biological tissue or liquid samples and for diagnosis of the condition of a mammalian biological tissue or liquid employing electrical resistance measurements.

SUMMARY OF THE INVENTION

One aspect of the invention is an apparatus for simultaneously obtaining a sample of mammalian biological tissue or liquid and measuring the electrical resistance of the tissue or liquid at at least two different frequencies for the purpose of diagnosis of the condition of the tissue or liquid, comprising: a main case, comprising a tube and demountable handle; a hook attached to the tube, comprising a pointed end, for obtaining a sample of the biological tissue and for serving as a passive electrode in contact with the biological tissue; an aspirating needle at least partially inside the tube, for obtaining a sample of the biological liquid and for serving as an active electrode in contact with the biological liquid or tissue; a liquid collector, connected to the aspirating needle, comprising a metal conductor in contact with the biological liquid and a piston, which at the determination of the condition of the biological liquid the needle executes the role of active electrode, and the metal conductor executes the role of passive electrode; an electroimpedancemeter electrically connected to the active and passive electrodes, for simultaneous measurement of the electrical resistance at at least two different frequencies; and an electrical plug, located in the handle and connected by electrical leads with the main case or hook and with the needle and in one embodiment to the syringe metal conductor, the electrical plug allowing electrical connection with an electroimpedancemeter. In one embodiment of the apparatus, the liquid collector is a syringe. In one embodiment of the apparatus, the electroimpedancemeter comprises: a source of alternating current voltage consisting of two generators, one for a first frequency voltage and the other for a second, higher frequency voltage. In a preferred embodiment, the first frequency is in the range from about 0.5 to about 10 kHz. In another preferred embodiment, the first frequency is in the range from about 1 to about 5 kHz. In another preferred embodiment, the first frequency is in the range from about 1 to about 3 kHz. In another preferred embodiment, the second frequency is in the range from about 10 to about 1000 kHz. In another preferred embodiment, the second frequency is in the range from about 20 to about 500 kHz. In another preferred embodiment, the second frequency is in the range from about 50 to about 300 kHz. In yet another preferred embodiment, there is a factor of at least 10× in kHz between the first and second frequencies. In another embodiment of the electroimpedancemeter of the apparatus, wherein the electroimpedancemeter comprises a source of alternating current voltage consisting of two generators, one for a first frequency voltage and one for a second frequency voltage, the electroimpedancemeter further comprises a voltage sum-up unit, the output voltage of which the first frequency voltage and second frequency voltage are present, serving for elimination of temporal intervals between moments of measurement of electrical resistance at first and second frequencies. In another embodiment, the aforementioned electroimpedancemeter further comprises a negative feedback circuit, comprising a rectifier and a filter of the first frequency for elimination of pulsations in the target voltage of the rectifier. In another embodiment, the aforementioned electroimpedancemeter further comprises a stabilized source of current, enabling the standardization of a measuring current proceeding through the biological tissue or liquid. In another embodiment, the aforementioned electroimpedancemeter further comprises an amplifier having an input and an output. In another embodiment, the aforementioned electroimpedancemeter further comprises a filter of the first frequency and a filter of the second frequency. In another embodiment, the aforementioned electroimpedancemeter further comprises a detector of the first frequency which produces a first output voltage and a detector of the second frequency which produces a second output voltage. In another embodiment, the aforementioned electroimpedancemeter further comprises a converter to divide the first output voltage by the second output voltage and a digital display having an input for displaying the output of the converter. In another embodiment, the aforementioned electroimpedancemeter further comprises a source of independent power. In a preferred embodiment, the electroimpedancemeter wherein: the outputs of the generators of first and second frequency voltage are connected to inputs of the sum-up unit. In a preferred embodiment, the electroimpedancemeter wherein: the output of the sum-up unit is directed through the rectifier and the filter of first frequency of the negative feedback circuit and is thereafter connected to the inputs of the generators of the first and second frequency voltage. In a preferred embodiment, the electroimpedancemeter wherein: the output of the sum-up unit is directed through the stabilized source of current and is connected with the active electrode. In a preferred embodiment, the electroimpedancemeter wherein: the active electrode is connected with the input of the amplifier. In a preferred embodiment, the electroimpedancemeter wherein: the output of the amplifier is connected with the inputs of the filters of first and second frequency, the outputs of which are connected accordingly with the inputs of the detectors of first and second frequency. In a preferred embodiment, the electroimpedancemeter wherein: the outputs of said detectors of first and second frequency are connected to the respective inputs of the converter. In a preferred embodiment, the electroimpedancemeter wherein: the outputs of the converter are connected to the inputs of the digital display.

In another aspect of the invention, a method is provided for simultaneously obtaining a sample of biological tissue and measuring the electrical resistance of the tissue at at least two different frequencies for the purpose of diagnosis of the condition of the tissue comprising the steps of: moving a tube into a space containing the biological tissue; contacting the biological tissue with an active and passive electrode; measuring the electrical resistance of the biological tissue at at least two different frequencies with an electroimpedancemeter; obtaining a sample of the biological tissue with the active and passive electrodes; and moving the tube containing the sample away from the space. In a preferred embodiment of the method, the tissue is bronchopulmonary tissue and the condition is benign or malignant tissue growth. Preferably, the malignant tissue growth is bronchus cancer. In another preferred embodiment of the method, the tissue is gastric mucosa and the condition is benign or malignant tissue growth or chronic inflammation. Preferably, the malignant tissue growth is gastroenteric cancer. In another preferred embodiment of the method, the tissue is thyroid tissue and the condition is benign or malignant tissue growth. Preferably, the malignant tissue growth is thyroid cancer. In another preferred embodiment of the method, the tissue is breast tissue and the condition is benign or malignant growth. Preferably, the malignant growth is breast cancer. In another preferred embodiment of the method, the tissue is larynx tissue and the condition is benign or malignant tissue growth. Preferably, the malignant tissue growth is larynx cancer. In yet another preferred embodiment of the method, the tissue is soft tissue and the condition is healthy or thermally injured. In another prefered embodiment of the method, the at least two different frequencies comprise a first frequency in the range from about 0.5 to about 10 kHz, and a second frequency in the range from about 10 to about 1000 kHz. Preferably, the first frequency is in the range from about 1 to about 5 kHz, and the second frequency is in the range from about 20 to about 500 kHz. More preferably, the first frequency is in the range from about 1 to about 3 kHz, and the second frequency is in the range from about 50 to about 300 kHz. In another preferred embodiment of the method, a lower of the at least two different frequencies is a first frequency and a higher of the at least two different frequencies is a second frequency, and there is a factor of at least 10× in kHz between the first and second frequencies.

In another aspect of the invention, a method is provided for simultaneously obtaining a sample of biological liquid and measuring the electrical resistance of the liquid at at least two different frequencies for the purpose of diagnosis of the condition of the liquid comprising the steps of: inserting a tube into the biological liquid; contacting the biological liquid with an active and passive electrode; withdrawing a sample of the biological liquid with an aspirating needle into the syringe; moving the tube out of the biological liquid; and measuring in the syringe the electrical resistance at at least two different frequencies of the biological liquid with an electroimpedancemeter. In a preferred embodiment of the method, the liquid is human blood and the condition is acute blood loss. In another preferred embodiment of the method, the liquid is human blood and the condition is selected from the group consisting of: alkaline reserve of blood, globular volume of blood, total circulating plasma, total circulating protein, volume of circulating erythrocytes, hematocrit number, blood alcohol, drug and anaesthetic content. In another preferred embodiment of the method, the liquid is human milk and the condition is lactostasis or mastitis. In another preferred embodiment of the method, the at least two different frequencies comprise a first frequency in the range from about 0.5 to about 10 kHz, and a second frequency in the range from about 10 to about 1000 kHz. More preferably, the first frequency is in the range from about 1 to about 5 kHz, and the second frequency is in the range from about 20 to about 500 kHz. More preferably, the first frequency is in the range from about 1 to about 3 kHz, and the second frequency is in the range from about 50 to about 300 kHz. In another preferred embodiment of the method, a lower of the at least two different frequencies is a first frequency and a higher of the at least two different frequencies is a second frequency, and there is a factor of at least 10× in kHz between the first and second frequencies.

In another aspect of the invention, an apparatus is provided for simultaneously obtaining a sample of mammalian biological tissue or liquid and measuring the electrical resistance of the tissue or liquid at at least two different frequencies for the purpose of diagnosis of the condition of the tissue or liquid, comprising: a main case, comprising a tube and demountable handle, the tube being insertable at one end into the demountable handle of gun or other type, the tube comprising corrosion-proof medical steel or other conventional material suitable for medical diagnostic use, the tube having at least one hole at one end; a protective casing which fits over the tube, is demountable and comprises a ring and spring-ball for fixing the spring-ball location of the casing at the hole, the location representing a maximum forward position or maximum reverse position of the casing; a hook comprising a pointed end, fixed at one end of the tube away from the handle and extending from the end for obtaining a sample of the biological tissue and for serving as a passive electrode in contact with the biological tissue; an aspirating needle, located inside the tube, the distal end of said needle extending from the end of the tube away from the handle, for obtaining a sample of the biological liquid and for serving as an active electrode in contact with the biological liquid or tissue, the proximal end of the needle being finished by a metal flange for jointing with a metal-glass syringe inside the main case handle; a metal-glass syringe, consisting of a glass flask, metal conic tip and metal piston, which at the determination of a condition of the biological liquid the metal tip executes a role of active electrode, and the metal piston executes a role of passive electrode; a fixing unit, located inside the tube and serving simultaneously to fix the hook at one end of the tube away from the handle and to isolate the area of the biological tissue or liquid; an electroimpedancemeter electrically connected to the active and passive electrodes, for simultaneous measurement of complete electrical resistance at at least two different frequencies; and an electrical plug, located in the handle and connected by electrical leads with the main case and the needle and optionally to said syringe metal piston, the electrical plug allowing electrical connection with an electroimpedancemeter. In one embodiment of the apparatus, the electroimpedancemeter further comprises: a source of alternating current voltage consisting of two generators, one for a first frequency voltage and one for a second, preferably higher, frequency voltage. In another embodiment of the electroimpedancemeter of the apparatus, wherein the electroimpedancemeter comprises a source of alternating current voltage consisting of two generators, one for a first frequency voltage and the other for a second frequency voltage, the electroimpedancemeter further comprises a voltage sum-up unit, the output voltage of which the first frequency voltage and second frequency voltage are present, serving for elimination of temporal intervals between moments of measurement of electrical resistance at first and second frequencies. In another embodiment, the aforementioned electroimpedancemeter farther comprises a negative feedback circuit, comprising a rectifier and a filter of the first frequency for elimination of pulsations in the target voltage of the rectifier. In another embodiment, the aforementioned electroimpedancemeter further comprises a stabilized source of current, enabling the standardization of a measuring current proceeding through the biological tissue or liquid. In another embodiment, the aforementioned electroimpedancemeter further comprises an amplifier having an input and an output. In another embodiment, the aforementioned electroimpedancemeter further comprises a filter of the first frequency and a filter of the second frequency. In another embodiment, the aforementioned electroimpedancemeter further comprises a detector of the first frequency which produces a first output voltage and a detector of the second frequency which produces a second output voltage. In another embodiment, the aforementioned electroimpedancemeter further comprises a converter to divide the first output voltage by the second output voltage and a digital display having an input for displaying the output of the converter. In another embodiment, the aforementioned electroimpedancemeter further comprises a source of independent power.

In another aspect of the invention, an apparatus is provided for simultaneously obtaining a sample of biological tissue and measuring the electrical resistance of the tissue at at least two different frequencies for the purpose of diagnosis of the condition of the tissue, comprising: a flexible electrode probe comprising a cable and an electrode tip, wherein the tip comprises an active electrode and passive electrode for simultaneously obtaining the sample of biological tissue and measuring the electrical resistance of the tissue; and an electroimpedancemeter electrically connected to the active and passive electrodes, for simultaneous measurement of complete electrical resistance at at least two different frequencies. In one embodiment, the apparatus further comprises an endoscope with a channel, wherein the flexible electrode probe fits inside the channel. In another embodiment, the apparatus further comprises a holder, used to hold the flexible electrode probe in direct contact with the skin of a finger.

In another aspect of the invention, a method is provided for simultaneously obtaining a sample of biological tissue and measuring electrical resistance of the tissue at at least two different frequencies for the purpose of diagnosis of a condition of the tissue comprising the steps of: placing a flexible electrode probe into a space containing the biological tissue; contacting the biological tissue with an active and a passive electrode; measuring the electrical resistance of the biological tissue at at least two different frequencies with an electroimpedancemeter; obtaining the sample of the biological tissue with the active and passive electrodes; and moving the flexible eletrode probe containing the sample away from the space. In one embodiment of the method, the placing is facilitated with an endoscope with a channel, wherein the flexible electrode probe fits inside the channel. In another embodiment of the method, the placing is facilitated with a holder, used to hold the flexible electrode probe in direct contact with the skin of a finger. In another embodiment of the method, the condition is selected from the group consisting of blood alcohol, drug and anaesthetic content.

In another aspect of the invention, a method is provided for comparative diagnosis of the condition of two biological liquids, comprising the steps of: placing a first biological liquid in a first liquid chamber; placing a second biological liquid in a second liquid chamber; measuring the electrical impedance at at least two different frequencies of the first and second liquids sequentially or simultaneously; and comparing the electrical resistance measurements of the first and second liquids. In one embodiment of the method, each of the two biological liquids is human breast milk, wherein the first biological liquid is from one breast and the second biological liquid is from the second breast.

BRIEF DESCRIPTION OF THE DRAWINGS

FIG. 6 illustrates an embodiment of the flexible electrode probe of the invention.

FIG. 7 illustrates an enlarged view of the coaxial cable electrode tip of the flexible electrode probe of the invention illustrated in FIG. 6.

FIG. 8 illustrates an enlarged end-on view of the coaxial electrode tip of the flexible electrode probe of the invention illustrated in FIG. 6.

DETAILED DESCRIPTION OF THE PREFERRED EMBODIMENT

Figure 1:
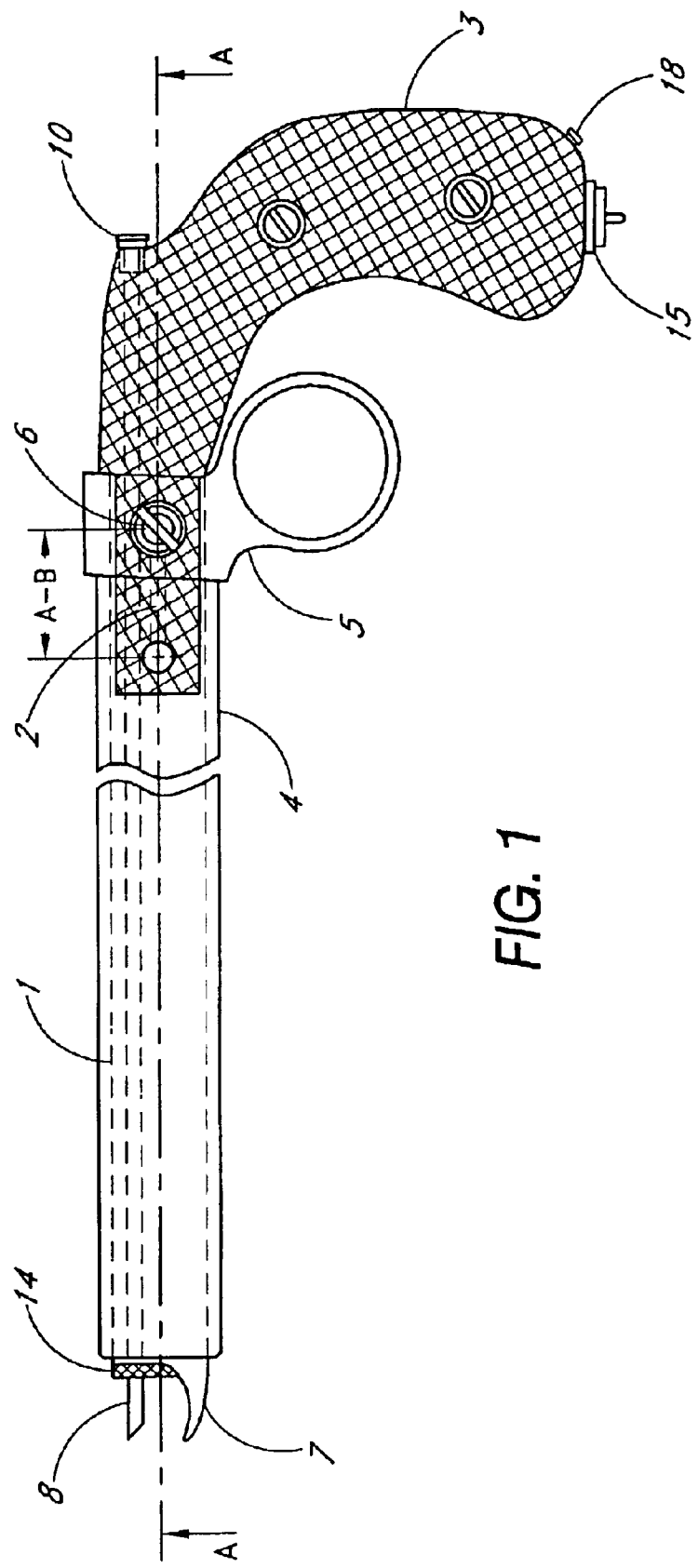
FIG. 1 is a general view of a preferred embodiment of the apparatus of the invention without the electroimpedancemeter.

The major objects of the present invention are an apparatus and method for simultaneously obtaining a sample of mammalian biological tissue or liquid and for measuring the complete electrical resistance of said biological tissue or liquid in-vivo (tissue) or ex-vivo (liquid) for the purpose of diagnosis of the condition of the tissue or liquid. The apparatus of the present invention comprises a biological tissue or liquid sampling apparatus and an electroimpedancemeter, or electrical impedance measuring device, allowing for the simultaneous measurement of complete electrical resistance at at least two different frequencies, or dispersion of resistance. The dispersion of resistance is a function of the state of the biological tissue or liquid. Thus, the apparatus and method of the present invention overcome the inherent precision and accuracy limitations of prior art devices used for the investigation of electrical parameters of biological tissues and liquids which at most relied upon serial measurements of resistance at low and high frequencies. The apparatus and method of the present invention also overcome the limitations in device versatility of prior art devices, which cannot simultaneously obtain a sample of biological tissue or liquid and measure dispersion of resistance. The apparatus and method of the present invention uniquely allow for obtaining a sample of a biological tissue or liquid and measurement of its electrical resistance at at least two different frequencies at the same precise location, thus providing the opportunity to gather more information from a single location and hence provide the opportunity for a more accurate diagnosis of the condition of the sample or organ or patient from which the sample derived. The apparatus and method of the present invention achieve this by the simultaneous usage of the sampling probes as electrodes for the simultaneous resistance measurements made at at least two different frequencies. An additional feature of the apparatus of the present invention is the minimal effect on the biological tissue or liquid of the measuring signal from the electroimpedancemeter. The apparatus of the invention is portable and relatively inexpensive. It permits the relatively rapid analysis of tissues in typically ½-10 minutes. The method of use and the equipment are easy and reliable in application. The apparatus can be used by average trained medical staff and additionally does not require special service.

The apparatus and method of the present invention applies to the general domain of clinical medicine and may be used to reveal the early forms of malignancies, bronchus cancer, gastroenteric cancer, thyroid cancer, breast cancer, larynx cancer, comedocarcinoma and soft tissue thermal injury. The present invention also allows one to determine the degree of acidity of gastric juice and to diagnose chronic forms of gastritis during endoscopy, to define the alkaline reserve of blood, blood volume and it's components and to diagnose and forecast the course of lactational mastitis.

The apparatus and method of the present invention may be utilized for measuring blood components such as alcohol, drugs and anaesthetics. Thus, the apparatus and method of the invention are suitable for blood alcohol or drug testing and are also suitable for determining the proper amount of anaesthetic to use, as well as to monitor the level of anaesthetic and to keep the level of anaesthetic constant.

The apparatus and method of the present invention may be utilized for man or animals, and is thus suitable for use with all mammals.

The apparatus of the present invention for simultaneously obtaining a sample of biological tissue or liquid and measuring the electrical resistance of the tissue or liquid at at least two different frequencies for the purpose of diagnosis of the condition of the tissue or liquid, comprises:

a. a main case, the main case comprising a tube and demountable handle;

b. a hook attached to the tube, the hook comprising a pointed end, for obtaining a sample of the biological tissue and for serving as a passive electrode in contact with the biological tissue;

c. an aspirating needle at least partially inside the tube, for obtaining a sample of the biological liquid and for serving as an active electrode in contact with the biological liquid or tissue;

d. a liquid collector, connected to the aspirating needle, comprising a metal conductor in contact with the biological liquid and a piston, which at the determination of the condition of the biological liquid the needle executes the role of active electrode, and the metal conductor executes the role of passive electrode;

e. an electroimpedancemeter electrically connected to the active and passive electrodes, for simultaneous measurement of the electrical resistance at at least two different frequencies; and f. an electrical plug, located in the handle and connected by electrical leads with the main case or hook and with the needle, and optionally to the syringe metal conductor, the electrical plug allowing electrical connection with an electroimpedancemeter.

A preferred embodiment of the apparatus of the present invention for simultaneously obtaining a sample of biological tissue or liquid and measuring the electrical resistance of the tissue or liquid at at least two different frequencies for the purpose of diagnosis of the condition of the tissue or liquid, comprises:

a. A main case, comprising a tube and demountable handle, the tube being insertable at one end into the demountable handle of gun or other type, the tube comprising corrosion-proof medical steel or other conventional material suitable for medical diagnostic use, the tube having at least one hole at one end;

b. A protective casing which fits over the tube, is demountable and comprises a ring and spring-ball for fixing the spring-ball location of the casing at the hole, the location representing a maximum forward position or maximum reverse position of the casing;

c. A hook comprising a pointed end, fixed at one end of the tube away from the handle and extending from the end for obtaining a sample of the biological tissue and for serving as a passive electrode in contact with the biological tissue;

d. A aspirating needle, located inside the tube, the distal end of the needle extending from the end of the tube away from the handle, for obtaining a sample of the biological liquid and for serving as an active electrode in contact with the biological liquid or tissue, the proximal end of the needle being finished by a metal flange for jointing with a metal-glass syringe inside the main case handle;

e. A metal-glass syringe, consisting of a glass flask, metal conic tip and metal piston, which at the determination of a condition of the biological liquid the metal tip executes a role of active electrode, and the metal piston executes a role of passive electrode;

f. A fixing unit, located inside the tube and serving simultaneously to fix the hook at one end of the tube away from the handle and to isolate the area of the biological tissue or liquid;

g. A electroimpedancemeter electrically connected to the active and passive electrodes, for simultaneous measurement of complete electrical resistance at at least two different frequencies; and h. A electrical plug, located in the handle and connected by electrical leads with the main case and the needle and optionally to the syringe metal piston, the electrical plug allowing electrical connection with an electroimpedancemeter.

Another embodiment of the apparatus of the present invention for simultaneously obtaining a sample of biological tissue and measuring the electrical resistance of the tissue at at least two different frequencies for the purpose of diagnosis of the condition of the tissue, comprises:

a. a flexible electrode probe comprising a cable and an electrode tip, wherein the tip comprises an active electrode and passive electrode for simultaneously obtaining the sample of biological tissue and measuring the electrical resistance of the tissue; and b. an electroimpedancemeter electrically connected to the active and passive electrodes, for simultaneous measurement of complete electrical resistance at at least two different frequencies.

The apparatus of the invention comprising a flexible electrode probe may be utilized in combination with an endoscope with a channel. The flexible electrode probe is inserted into the endoscope channel so that simultaneous sampling and impedance readings of biological tissues such as gastrointestinal tissues may be taken in locations which are inaccessible to other prior art devices. Alternatively, the aforementioned apparatus of the invention with a flexible electrode probe may be combined with a thimble-like support part at the distal end of the flexible electrode probe which contains the electrode tip comprising active and passive electrodes. The thimble-like part can be placed over a finger to hold the active and passive electrodes in place in direct contact with the skin of a finger or fingertip. In this way, secure monitoring of electrical impedance can take place as well as sampling of the tissue of the finger or fingertip. The aforementioned apparatus is particularly useful for monitoring of the electrical impedance of blood for the purpose of determining blood alcohol content or drug content in the blood. It is also useful for determining the amount of anaesthetic utilized during an anaesthesia procedure. It can be utilized to determine the proper amount of anaesthetic to utilize prior to the anaesthesia procedure as well as to keep the amount of anaesthetic utilized over a period of time constant with the additional use of a feedback apparatus which sends a signal from the electroimpedancemeter to the device controlling the delivery of the anaesthetic.

The electroimpedancemeter is used to measure impedance at a "low" frequency which is preferably in the range from about 0.5 to about 10 kHz, more preferably in the range from about 1 to about 5 kHz, and still more preferably in the range from about 1 to about 3 kHz. The electroimpedancemeter also is used to measure impedance at a "high" frequency which is preferably in the range from about 10 to about 1000 kHz, more preferably in the range from about 20 to about 500 kHz, and still more preferably in the range from about 50 to about 300 kHz. It is preferred that there be a factor of at least 10× between the low and high frequencies, although this is not a requirement for all measurements. In the preferred embodiment presented in the present detailed description of the invention, the ratio between the two frequencies is 100×. In other embodiments of the present invention, more than two frequencies can be measured simultaneously. In such embodiments, the selection of the first two frequencies should be as described above and additional frequencies preferably spaced at logarithmic (or 10× in kHz) intervals.

The electroimpedancemeter of the apparatus of the present invention comprises:

a. A source of alternating current voltage consisting of two generators, one for a first frequency voltage and the other for a second frequency voltage;

b. A voltage sum-up unit, the output voltage of which the components of said low frequency voltage and high frequency voltage are present, serving for elimination of temporal intervals between moments of resistance measurements at low and high frequency;

c. A negative feedback circuit, comprising a rectifier and a filter of low frequency for elimination of pulsations in the target voltage of the rectifier;

d. A stabilized source of current, enabling the standardization of a measuring current proceeding through said biological tissue or liquid;

e. An amplifier, f. A filter of low frequency and a filter of high frequency;

g. A low frequency detector and a high frequency detector;

h. A converter to divide said low frequency detector voltage output by said high frequency detector voltage output, such as an analog-digital converter, i. A digital display for displaying the output of said converter;

j. A source of independent power.

Figure 2:
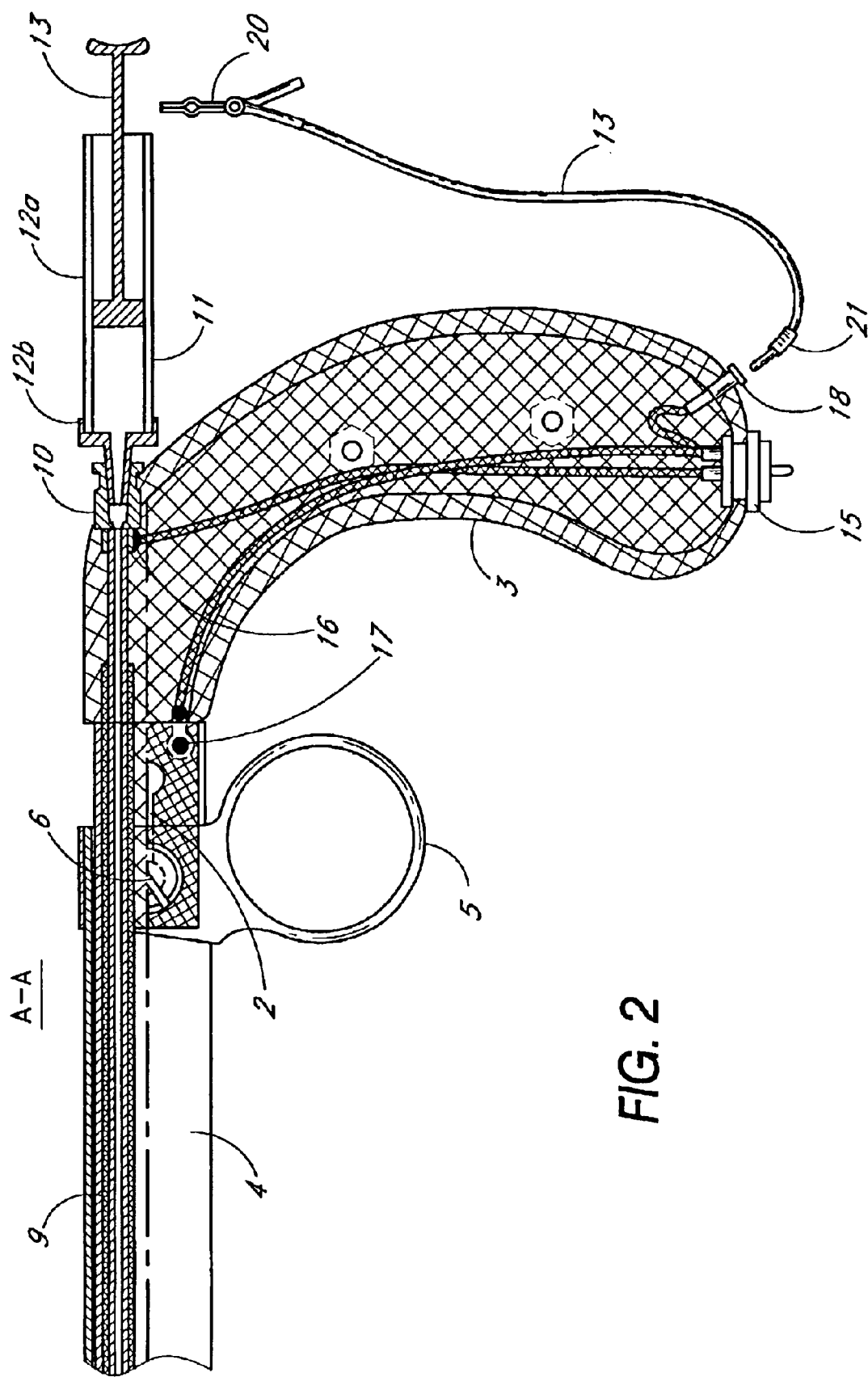
FIG. 2 is an expanded external and internal view of the embodiment of the apparatus of the invention illustrated in FIG. 1.
Figure 3:
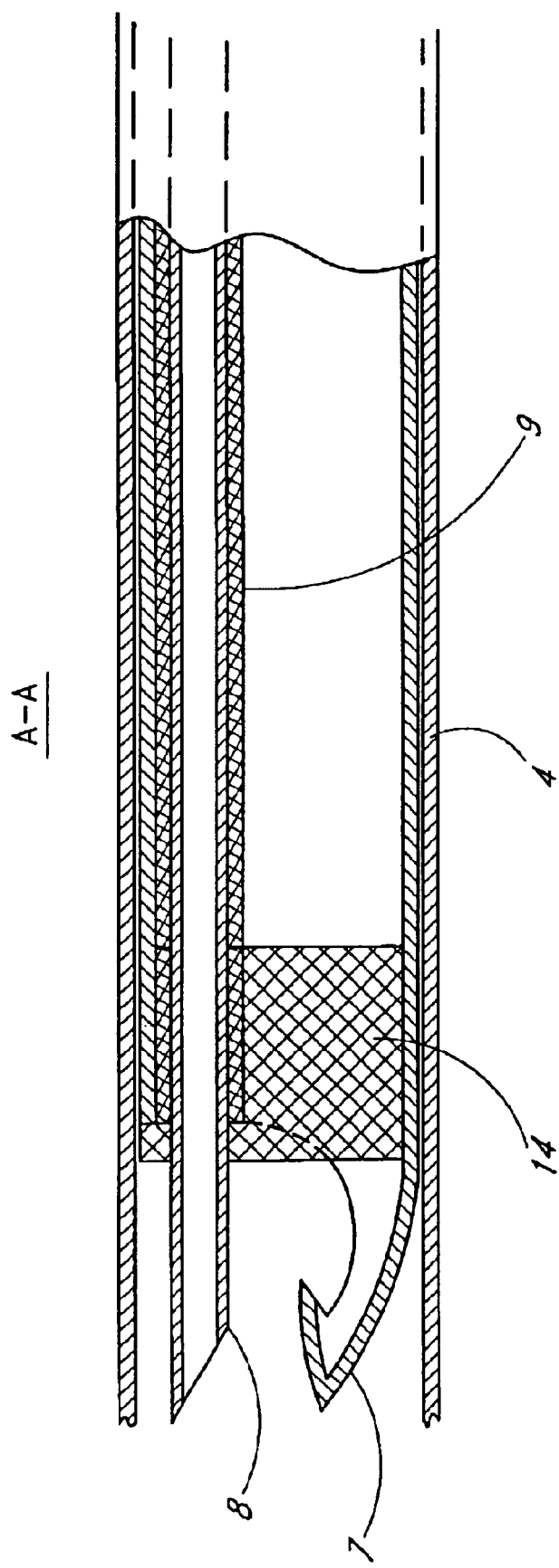
FIG. 3 is a view of the embodiment of the apparatus of the invention illustrated in FIG. 1 with pull-out protective casing and opened instrument with sampling probe for research.

A preferred embodiment of part of the apparatus of the present invention for simultaneously obtaining a sample of biological tissue or liquid and measuring the electrical resistance of the tissue or liquid at least two different frequencies for the purpose of diagnosis of the condition of the tissue or liquid, without the electroimpedancemeter, is illustrated in FIGS. 1–3. FIG. 1 is a general view of a preferred embodiment of the apparatus of the present invention without the electroimpedancemeter. FIG. 1 illustrates a multifunctional tool, comprising: a main case tube 1, executed from corrosion-proof medical steel and a main case demountable handle 3 of gun-type, consisting of two halves, tube 1 being insertable at one end into demountable handle 3. Tube 1 has a hole in the forum of slot 2 at the end which is insertable into handle 3. There is an enlarged hole at each end of slot 2. A protective casing 4 fits over tube 1. Casing 4 is demountable and supplied with a ring 5 and spring-ball 6 for fixing the spring-ball location of casing 4 at the hole at either end of slot 2 in tube 1, this location representing a maximum forward position A or maximum reverse position B of the casing 4. Hook 7 has a pointed end, is electrically conductive and is utilized for sampling biological tissue and also as the passive electrode in contact with the biological tissue for the resistance measurements. Hook 7 is fixed at one end of tube 1 away from handle 3 and extends from the end of tube 1. Aspirating needle 8 is located inside tube 1. The distal end of needle 8 extends from the end of tube I away from handle 3 and is utilized for sampling biological liquid and serves additionally as an active electrode in contact with the biological tissue or liquid. Needle 8 is electrically isolated by isolating tubing 9, illustrated in FIG. 3. The proximal end of needle 8 is rigidly fixed in handle 3 and finished with a metal flange 10 (FIGS. 1 and 2) for jointing with a metal-glass syringe 11 (FIG. 2), consisting of a glass flask 12a, metal conic tip 12b and metal piston 13 (FIG. 2). Fixing unit 14 (FIG. 3), located in case 1, fixes the position of needle 8 and performs simultaneously the role of isolator. Electrical plug 15 (FIG. 2) is located in the bottom part of handle 3. Lead 16 is soldered to needle 8 and connected to plug 15. Lead 17 is soldered to case 1 and connected to the high frequency leg of plug 15. The additional contact-jack 18 is connected to the mass of plug 15.

Resistance measurements of sampled biological liquids are made with lead 19 with clamp 20 connected to metal piston 13 and probe 21 (FIG. 2) inserted into contact-jack 18. Here the metal conic tip 12b serves as active electrode, and metal piston 13—as passive electrode. Flange 10 is closed with a special cap when syringe 11 is not attached to the flange (not shown).

Note that in other embodiments of the part of the apparatus of the present invention without the electroimpedancemeter, conventional flexible materials suitable for medical diagnostic use can be employed for any or all parts of the aforementioned apparatus so that the apparatus itself may be flexible and thus may be used under medical diagnostic situations requiring a flexible apparatus. It is to be understood that all electrical connections will be maintained with the aforementioned flexible apparatus. For example, a metal needle connected with flexible tubing to the syringe can be electrically connected with the syringe and the apparatus with electrical wire. Similarly, electrical connections with the hook can be made with electrical wire.

It is not necessary to use a protective casing or fixing unit as described above. Other conventional means can also be employed to allow the apparatus of the present invention without the electroimpedancemeter to perform its functions properly. For example, other means of operating the hook for obtaining a sample of biological tissue may be employed with the present invention. As an example, the hook may be operated with an electromechanical device such as a solenoid suitably connected to a piston, or piston, pivot and lever. The electrical connection between the hook itself, which serves as the passive electrode, and the remainder of the apparatus can be made with electrical wire. In this instance, the tube of the apparatus may serve as the protective casing and the protective casing with the ring and spring ball is not necessary.

Additionally, it is not necessary to use a glass syringe with a metal tip and metal piston. A plastic syringe can also be employed with conventional tip and piston. In this latter case, a metal conductor in contact with the biological liquid inside the syringe can be employed. In this case, the metal needle serves as the active electrode and metal conductor as passive electrode. Resistance measurements of sampled biological liquids are then made with lead 19 with clamp 20 connected to the metal conductor and probe 21 (FIG. 2) inserted into contact-jack 18. Any other suitable liquid collector can also be employed, as long as all functional and electrical requirements are met.

Figure 4:
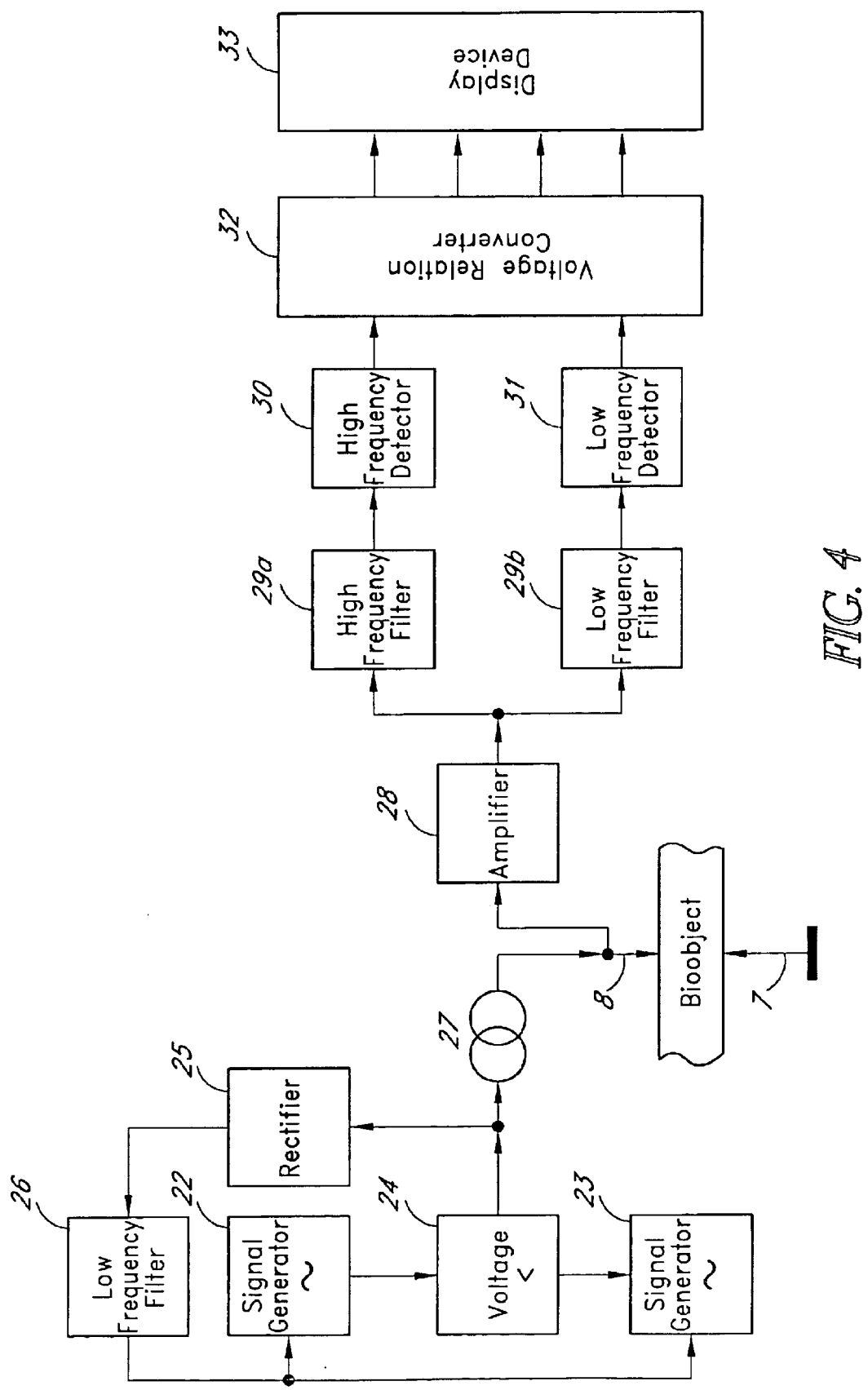
FIG. 4 is a block diagram of one embodiment of the electroimpedancemeter of the invention.

On FIG. 4 is shown one embodiment of the electroimpedancemeter of the invention, including the source of low and high frequency alternating current voltage consisting of two generators 22 and 23, a voltage sum-up unit 24, a rectifier of the negative feedback 25, a filter of low frequency of negative feedback 26, a stabilizer of measuring current 27 enabling the standardization of a measuring current proceeding through a biological tissue or liquid, amplifier 28, a filter of high frequency 29a, a filter of low frequency 29b, a detector of high frequency 30, a detector of low frequency 31, converter of the voltages' relation 32, a digital display device 33 and source of independent power (not shown). The outputs of generators of low and high frequency, 22 and 23 respectively, are connected to inputs of the sum-up unit 24. The output of the sum-up unit 24 is directed through rectifier 25 and the filter of low frequency of negative feedback 26 and is thereafter connected to the inputs of the generators of high and low frequency, 22 and 23 respectively. The output of the sum-up unit 24 is directed through a stabilized source of current 27 and is connected with the active electrode 8. The active electrode 8 is connected with the input of the amplifier 28. A passive electrode 7 is connected to ground as well as the biological object being measured. The output of the amplifier 28 is connected with the inputs of the filters of low and high frequency, 29a and 29b respectively, the outputs of which are connected accordingly with the inputs of the detectors of low and high frequency, 30 and 31 respectively. The outputs of the detectors of low and high frequency 30 and 31 are connected to the respective inputs of the converter of the relation of voltage 32. This converter is a division unit whose output indicates the ratio of the low frequency detector output divided by the high frequency detector output. The converter is typically a conventional analog-to-digital converter. The outputs of the converter of the relation of voltage 32 are connected to the inputs of the digital display 33.

The two generators of low and high frequency 22 and 23 are provided for the elimination of a temporal interval between moments of measurements at low and high frequency. This is additionally achieved with the sum-up unit 24 which produces a target voltage which contains the components of low-frequency and high-frequency voltage of alternating current. The two generators of low and high frequency can produce various combinations of two frequencies, one of which is preferably a low frequency such as 2 kHz and the other of which is preferably a high frequency such as 200 kHz. The selection of the appropriate frequencies is as previously described and is known in the art. Preferably, there is at least a factor of 10× between the two frequencies, although this is not a requirement for all measurements. Other ratios between the two frequencies are also effective, as in the above, wherein a factor of 100× exists between 2 kHz and 200 kHz. The negative feedback circuit consisting of rectifier 25 and filter of low frequency 26 between the output of unit 24 and the inputs of generators 22 and 23 is included for stabilization of the amplitude of the target voltage of the sum-up unit 24. The filter of low frequency 26 is included for elimination of pulsations, present in the target voltage of rectifier 25. The stabilizer of the measuring current 27 insures that the measuring current proceeding through the biological tissue does not exceed the requirements of international standards. The amplification factor for amplifier 28 is generally about 5, but can be more or less depending upon the specific need.

Figure 5:
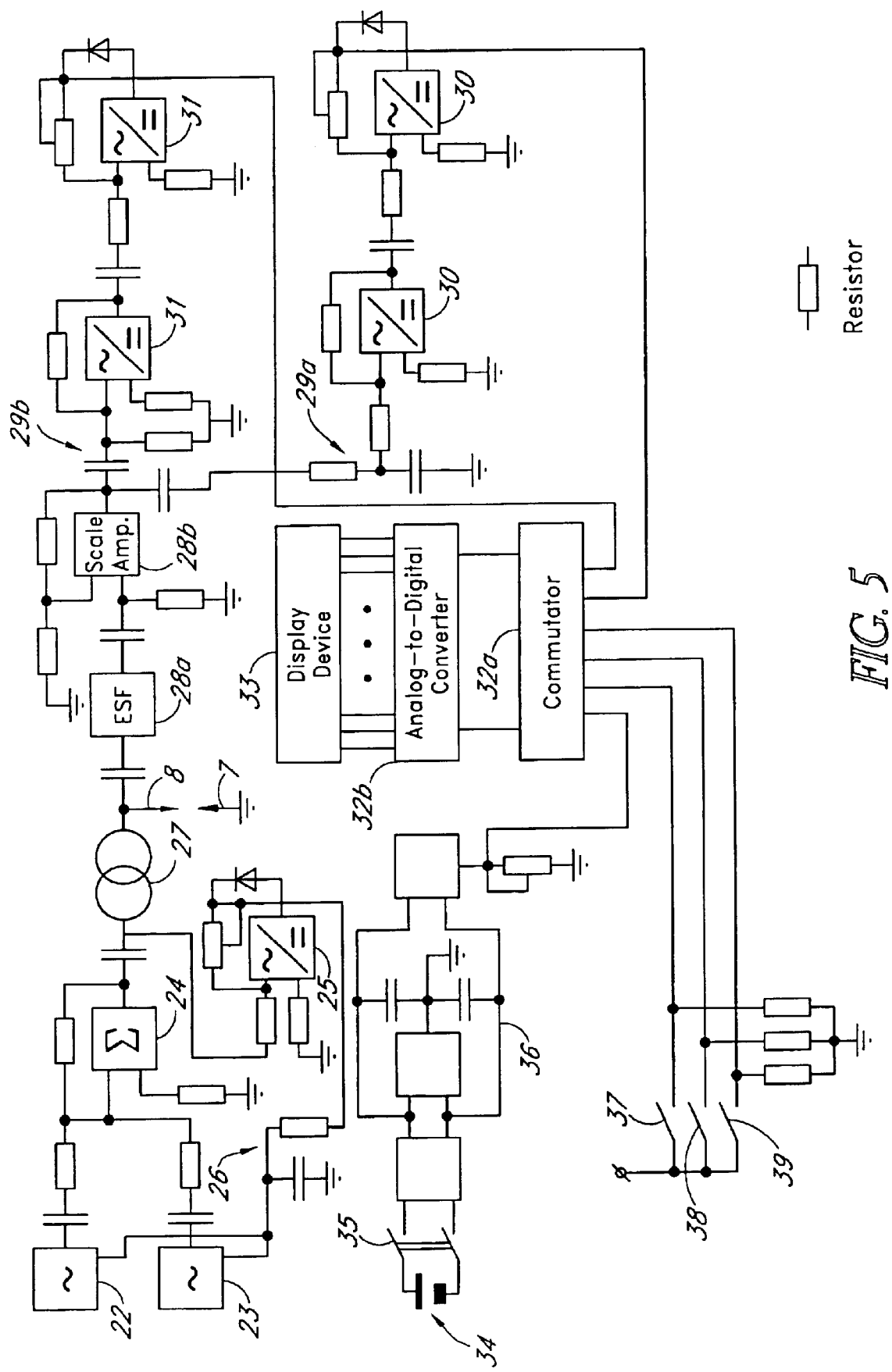
FIG. 5 is an electrical schematic-block diagram of a preferred embodiment of the electroimpedancemeter of the invention.

FIG. 5 is an electrical schematic-block diagram of a preferred embodiment of the electroimpedancemeter of the invention. Note that on this figure, the conventional electrical circuit symbol for an electrical resistor component is not employed. An electrical resistor component is represented by a small rectangular box with an electrical lead at either end. A variable resistor component is represented with the same symbol with the exception that a third electrical lead is connected to the center of the rectangular box. Components 7,8 and 22–33 are as described in FIG. 4, with 28a representing an ejector source follower part of the amplifier 28, the output of which is connected to the input of the scale amplifier 28b. Component 32a represents a commutator part of an analog-to-digital converter 32b. Additional components are as follows: component 34 is an independent power source, representing a 12 V battery, which is connected through a main power switch 35 to stabilizer circuitry 36 and thereafter to the commutator 32a. Components 37, 38 and 39 are switches which are part of the control circuitry of the analog-to-digital converter 32b, and are connected to converter 32b via commutator 32a. Component 37 is a switch for obtaining a readout on the digital display 33 of the high frequency resistance of the biological sample and component 38 is a switch for obtaining a readout on the digital display 33 of the low frequency resistance of the biological sample. Component 39 is a switch for obtaining a readout on the digital display of the polarizability, PC, or dispersion of resistance, of the biological sample.

Components of the above electroimpedancemeter can be conventional commercially available components and are known to those of ordinary skill in the construction of electrical devices. For example, digital display 33 is a conventional 4-digit liquid-crystal type digital indicator.

Typical technical parameters of the electroimpedancemeter are as follows: peak current consumed by the display panel: 8 mA; maximum power. 10 mW; source of independent power: one storage battery, 12 V; measuring current value: max. 10 mKA; and constant operating time: 4 hours.

An electroimpedancemeter according to the present invention can be constructed which can simultaneously measure more than two frequencies simultaneously. This can be accomplished with conventional parallel circuit design and construction methods, i.e., 3 frequency generators, 3 filters, 3 detectors, etc. would be employed for an electroimpedancemeter which measures 3 frequencies simultaneously. The method employing the apparatus of the present invention for simultaneously obtaining a sample of biological tissue and measuring the electrical resistance of the tissue at at least two different frequencies for the purpose of diagnosis of the condition of the tissue generally comprises the steps of:

a. Moving the tube into a space containing the biological tissue;
b. Contacting the biological tissue with the active and passive electrodes;
c. Measuring the electrical resistance of the biological tissue at at least two different frequencies with the electroimpedancemeter;
d. Obtaining a sample of biological tissue with the active and passive electrodes; and
e. Moving the tube containing the sample away from the space.

The method employing the apparatus of the present invention for simultaneously obtaining a sample of biological liquid and measuring the electrical resistance of the liquid at at least two different frequencies for the purpose of diagnosis of the condition of the liquid generally comprises the steps of:

a Inserting the tube into the biological liquid;
b. Contacting the biological liquid with the active and passive electrode;
c. Withdrawing a sample of the biological liquid with the aspirating needle into the syringe;
d. Moving the tube out of the biological liquid; and
e. Measuring in the syringe cell the electrical resistance at at least two different frequencies of the biological liquid with the electroimpedancemeter.

The preferred apparatus of the invention illustrated in FIGS. 1–4 is utilized according to the method of the invention in the following manner: holding handle 3, the researcher with forefinger inside ring 5 moves casing 4 along the line of arrow A-B (FIG. 1). The moving of casing 4 is limited by the length of slot 2 in main case tube 1, so as the distal part of casing 4 is moved forward to position A, it completely overlaps elements 7 and 8. Thus casing 4 takes a position at which the tool for sampling the material (tissue, liquid) is completely closed—with the purpose of minimal traumatizing of internal tissues (the distal edge of casing are smoothed). The researcher then introduces the distal end of the apparatus into the body at the location to be studied. Hook 7 serves for optionally clasping one piece of biological tissue, and the needle 8, to be inserted inside the tissue fixes the location of the apparatus for sampling and is also utilized for the optional sampling of biological liquids.

At the moment of sampling, initiated by a gentle forward push on handle 3, casing 4 comes back to the position "B," and after this manipulation again approaches elements 7 and 8 in position "A", promoting thus the tear-off of a piece of biological tissue by book 7.

In the moment of touching of the biological tissue or liquid by needle 8 and hook 7 the electrimpedancemeter transfers a measuring signal from the output of a stabilizer 27 through the passive and active electrodes—hook 7 and needle 8 respectively. Simultaneously, a measuring signal or current of high and low frequency penetrates into the cell structures of the biological tissue. As the variable measuring current flows through the tissue a power failure between electrodes 7 and 8 occurs, proportional to a module of complete electrical resistance of the tissue. The power loss arrives simultaneously at the amplifier 28 and thereafter at the inputs of filters of low and high frequency 29$a$ and 29$b$, the outputs of which constitute a variable voltage which arrives at the inputs of detectors 30 and 31. A constant voltage, proportional to resistance ZHf, is formed at the output of the detector of high frequency 30. Similarly, a constant voltage, proportional to resistance ZLf, is formed at the output of the detector of low frequency 31. The outputs of detectors 30 and 31 are input into the analog-digital converter 32, the output of which is a ratio of the low frequency detector output voltage divided by the high frequency detector output voltage and which constitutes the digital information about the factor of tissue polarization.

After the completion of sampling the apparatus together with protective casing 4 is removed from the body, following which casing 4 is removed from main case tube 1. The selected piece of tissue will then be passed for histological research.

The aspirating needle 8 for sampling a biological liquid is used in the following manner: the protecting cap is removed from flange 10, and the syringe 11 by tip 12$b$ is tightly inserted into flange 10. Piston 13 is initially in the input position (is maximally proximate to tip 12$b$). The liquid from a body is then aspirated in the syringe in a volume of about 0.5 to about 2 milliliters in the conventional manner by withdrawing piston 13.

Resistance measurements on the aforementioned biological liquids are made as previously described in the following manner: clamp 20 is connected to the acting end of metal piston 13 and probe 21 is inserted into jack 18. In the "closed" electrical circuit the syringe 11 with metal piston 13 and tip 12$b$ serves as a cell, in which the metal tip 12$b$ serves as active electrode and piston 13—as passive electrode. In other words—syringe 11 with tip 12$b$ provides reliable electrical contact with the flange 10, and lead 19, connected by clamp 20 with piston 13 and inserted in jack 18 by leg 21 allows the measurement of specific resistance in the volume of the syringe cell 11 (in the volume of 2 milliliters). All of the measurements of specific resistance of a biological liquid in the syringe cell 11 are carried out similarly to measurements of specific resistance on biological tissue.

The embodiment of the apparatus of the invention shown in FIGS. 1–3 cannot be used to diagnose particular locations of gastrointestinal tissue which are a substantial distance inside the body. In consideration of this unmet need, it has been discovered that a flexible electrode probe can be utilized in combination with an endoscope with a channel and an electroimpedancemeter of the invention to simultaneously obtain a tissue sample and take impedance readings of the tissue sample in locations deep inside the body. This apparatus is particularly well suited to sample and measure gastrointestinal tissue deep inside the body. FIGS. 6, 7, and 8 illustrate an embodiment of a flexible electrode probe which has been developed for this purpose. The flexible electrode probe illustrated in FIGS. 6–8 can be used in combination with the apparatus of the invention illustrated in FIG. 5 to carry out the method of the invention for simultaneously obtaining a sample of biological tissue and measuring the electrical resistance of the tissue at at least two different frequencies for the purpose of diagnosis of the condition of the tissue. In this case, a sample of tissue approximately corresponding to a needle biopsy is taken by the flexible electrode probe illustrated in FIGS. 6–8.

FIG. 6 illustrates the flexible electrode probe 10. The flexible electrode probe 10 comprises a flexible coaxial electrical cable consisting of two separate electrical wires or cables. A coaxial cable connector 30 is used to connect the coaxial electrode cable comprising an external coaxial cable 40 and an internal coaxial cable 45 to the input of the electrical apparatus of the invention illustrated in FIG. 5. External coaxial cable 40 is connected to the coaxial cable connector 30 and is in continuous electrical connection with the internal coaxial cable 45 as well as the coaxial connector 30. The coaxial cable connector 30 is adjacent to rubber protectors 41 and 42, which are placed over external coaxial cable 40 and are utilized to protect the external coaxial cable 40 from damage due to bending, twisting and flexing motions during normal usage. The external coaxial cable 40 is continuously outside the body and is not inserted inside a channel of an endoscope. The external coaxial cable 40 is generally from 10–150 cm in length. Preferably, it is between about 25 and 100 cm in length. Most preferably, the external coaxial cable 40 is about 50 cm in length. An endoscope channel stop 50 is placed on the outside of the distal end of the external coaxial cable 40. The purpose of the endoscope channel stop 50 is to prevent the external coaxial cable 40 from entering the endoscope channel (not shown). The endoscope channel stop 50 controls the amount of the internal coaxial cable 45 that is placed inside the endoscope channel. The endoscope channel stop 50 may be moveable in alternative embodiments of the flexible electrode probe 10. A rubber cable protector 43 is placed on the outside of the external coaxial cable 40 adjacent to the endoscope channel stop 50 and is utilized to protect the external coaxial cable 40 from damage due to bending, twisting and flexing motions at this location during normal usage. Adjacent to the endoscope channel stop 50 is a spring protector 60, which is utilized to protect the internal coaxial cable 45 from bending, twisting and flexing motions which may damage the cable. The internal coaxial cable 45 is generally between about 50 and 250 cm in length. Preferably, it is between about 100–200 cm in length. Most preferably, the internal coaxial cable 45 is about 150 cm in length. The internal coaxial cable 45 is connected at its distal end to a coaxial cable electrode tip 20.

The coaxial cable electrode tip 20 is shown in greater detail in a side view in FIG. 7. The coaxial cable electrode tip 20 consists of a first impedance electrode 21 and a second impedance electrode 25. Either of these impedance electrodes can represent either the passive electrode 7 or the active electrode 8 in the impedance circuitry illustrated in FIG. 5. Both impedance electrodes 21 and 25 are constructed generally of solid metal. The first impedance electrode 21 is in continuous electrical connection with a flexible coaxial electrode cable 22 which in turn is protected by a plastic insulation sheath 23. The approximate external diameter of the plastic sheath 23 is about 1.2 mm. The approximate external diameter of the first impedance electrode 21 is about 1 mm. Impedance electrode 21 is generally about 4 mm in total length from the distal end of the plastic insulation sheath 23 to the distal sharp tip of the impedance electrode 21. The second impedance electrode 25 is generally about 2 mm in length. The second impedance electrode 25 is placed inside a circular duct or channel (not shown) which is surrounded by the flexible coaxial electrode cable 22. There is no electrical contact between the first impedance electrode 21 and second impedance electrode 25 except through the biological sample between electrodes 21 and 25. This lack of electrical contact between electrodes 21 and 25 is maintained by an appropriate insulator placed between the two electrodes (not shown).

FIG. 8 illustrates an end-on view of the coaxial cable electrode tip 20. Shown in FIG. 8 are the first and second impedance electrodes 21 and 25 respectively. Also shown is plastic sheath 23 which surrounds both impedance electrodes 21 and 25. Not shown in this Figure is the electrode insulation maintained between electrodes 21 and 25 to prevent electrical connection between the two electrodes.

The first and second impedance electrodes 21 and 25 respectively, can also be utilized to take a biopsy of the tissue such as gastrointestinal tissue. Electrodes 21 and 25 are shaped for this purpose as well as to make the proper electrical contact with tissues so that a simultaneous impedance measurement can be taken.

The preferred method of the invention employing the flexible electrode probe 10 for obtaining a sample of gastrointestinal tissue and measuring the electrical resistance or impedance of the tissue comprises the steps of:

a. inserting the flexible electrode probe internal coaxial cable 45 inside an appropriate channel of an endoscope;

b. simultaneously contacting the tissue with the first and second impedance electrodes 21 and 25 respectively;

c. simultaneously measuring the electrical resistance of the tissue at at least two different frequencies with the electroimpedance meter of the invention illustrated in FIG. 5 and sampling the tissue with the sharp ends of the impedance electrodes 21 and 25; and d. moving the internal coaxial cable 45 containing the sample of tissue out of the channel of the endoscope.

In an alternative embodiment of the apparatus and method of the invention employing the flexible electrode probe 10 with coaxial cable electrode tip 20 and associated parts, the first and second impedance electrodes 21 and 25 may be retracted inside plastic sheath 23 following the sampling of biological tissue and completion of the impedance readings. This embodiment of the apparatus and method of the invention employing the flexible electrode probe 10 is made possible by insuring that the external diameter of the first impedance electrode 21 is smaller than the internal diameter of the plastic sheath 23, so that movement of the flexible coaxial electrode cable 22 is allowed inside of plastic sheath 23. In this way, a sample of biological tissue taken by the first and second impedance electrodes 21 and 25 respectively can be protected inside plastic sheath 23 following sampling. The sample therefore would not be lost following sampling and could be safely recovered for further histological analysis.

The entire construction of the flexible electrode probe 10 can be made with conventional plastic and metal materials which are known in the art. Also, the geometries of the various parts of flexible electrode probe 10 can be made appropriate to the particular endoscope and endoscope channel employed along with the flexible electrode probe 10, if an endoscope is used.

A general method of the invention employing a flexible electrode probe for simultaneously obtaining a sample of biological tissue and measuring electrical resistance of the tissue at at least two different frequencies for the purpose of diagnosis of a condition of the tissue comprises the steps of:

a. placing a flexible electrode probe into a space containing the biological tissue;

b. contacting the biological tissue with an active and a passive electrode;

c. measuring the electrical resistance of the biological tissue at at least two different frequencies with an electroimpedancemeter;

d. obtaining the sample of the biological tissue with the active and passive electrodes; and e. moving the flexible eletrode probe containing the sample away from the space.

Yet another method of the invention employs an impedance measuring cell with two separate chambers for holding biological liquids, wherein one chamber is filled with a control sample of biological liquid and the other chamber is filled with a test sample of biological liquid. Impedance measurements are taken sequentially or simultaneously of the liquids in the two chambers and compared. It has been discovered that in this way, smaller, more accurate and precise impedance difference measurements can be obtained. For example, a sample of breast milk from the left breast suspected to have a medical problem may be directly compared to a sample of breast milk from the right breast known to be healthy. This method of comparative diagnosis of biological liquids may also be performed with two or more separate cells, each with one liquid chamber, the number of cells corresponding to the number of biological liquids to be compared.

The following examples are provided by way of illustration only and are not intended as a limitation of the present invention, many variations of which are possible without departing from the spirit and scope thereof.

EXAMPLE 1

Diagnosis of Bronchopulmonary Tissue.

The embodiment of the apparatus of the invention shown in FIGS. 1–4 is used with the method of the invention to diagnose bronchopulmonary tissue. The casing 4, as shown in FIG. 3, is mounted on main case tube 1. While holding the handle 3, the researcher moves ring 5 and puts the casing 4 on the distal end of tube 1, thus blocking the sampling and electrode elements 7 and 8, and fixing the casing 4 in the slot 2 of tube 1 in the position "A." The apparatus consisting of the main case tube, casing and sampling and electrode elements is entered through a special tube of a bronchoscope under the control of sight. The apparatus is then included in the electrical circuit of the electroimpedancemeter shown in FIG. 4 through the switch plug 15.

After the tool has reached a necessary depth and the required location within the bronchial tract, the researcher puts off the casing 4 by ring 5 to position "B". By the hook 7, he tears off the piece of tissue, then again puts the protective casing 4 on the tool in position "A". At the moment of reliable contact of hook 7 and needle 8 with the bronchopulmonary tissue the electrical circuit of the electroimpedancemeter is completed, and through the electrodes 7 and 8 the measuring signal in a sun of voltage of alternating current of high and low frequency contacts the issue. Power decreasing between the electrodes 7 and 8 is proportional to the module of complete electrical resistance. The functional condition of the bronchopulmonary tissue is evaluated according to the relation of resistance measured at low frequency to resistance measured at high frequency, that is to a factor of polarization. A range of measurements from 20 up to 2000 Ohm includes main relative error.

$$+/- \left[2, 5 + 0, 25\left(\frac{Nlimiting}{Nmeasured} - 1\right)\right],$$

Where Nlimiting—top border of measurements range
Nmeasured—measured significance of resistance.

The summarized voltage of the alternating current, consisting of voltage of high frequency and voltage of low frequency, permits to avoid the loss of information in the interval between the measurements and is expressed by the formula:

$$Us = [UHf + ULf] \times Ks,$$

where Us is the target total voltage of the sum-up unit and Ks is the factor of amplification of the sum-up unit.

A direct voltage, proportional to the ZHf (f=200 kHz) resistivity, is formed on the outlet of the detector of high frequency 30, and the same process of formation of a direct voltage, proportional to the ZLf (f=2 kHz) resistivity, occurs at the outlet of the detector of low frequency 31. These voltages are input to the respective high and low frequency input channels of the converter 32. Digital information is formed in the output of the converter of the relation of voltage 32. The digital information is proportional to the relation of modules of complete resistance at low and high frequencies, that is, the digital information is proportional to the factor of polarization (FP) of bronchopulmonary tissue under the known formula:

$$FPtissue = \frac{ZLf}{ZHf}$$

Once the resistance measurements have been taken, the researcher under the control of eye removes the apparatus from the researched area, the protective casing is accurately removed, and the piece of bronchopulmonary tissue is transferred for histological research. The combined set of data from resistance measurements and histology test results can be compared with published data relating bronchopulmonary tissue status with serial resistance measurements and histology data. Alternatively, a new set of information can be generated which correlates simultaneous resistance measurements and histology test data with tissue status. The results of the above diagnostic procedure employing the apparatus and method of the present invention demonstrate that precise, accurate and simple diagnosis of bronchopulmonary tissue or other biological tissues and liquids can be achieved.

EXAMPLE 2

Diagnosis of Gastric Mucosal Tissue.

The embodiment of the apparatus of the invention shown in FIGS. 1–4 is used with the method of the invention according to Example 1 to diagnose a particular location on the gastric mucosa. Patient S., a 48 year old, is inspected outpatiently. Conventional gastroscopy is carried out. Flat ulcerous damage is visually detected in the antral portion of the stomach on the small curve side. Borders of the ulcer are indistinct, the ulcer base is fibrinous and infiltration of the gastric wall during instrumental palpation is not detected. The pylorus is clipped, has some deformation and it's mucous is hyperemic. The endoscopic diagnosis is an ulcer of the antral portion of the stomach. The apparatus of the invention as in Example 1 is entered through a separate tube of the endoscope and contacted with the tissue. Resistance measurements are taken in two opposite borders of the ulcer and expressed in terms of the polarizability, PC, of the tissue. The results follow:

Location 1: Hf=245 cm, Lf=440 cm
PC=440/245=1.8
Location 2: Hf=210 cm, Lf=390 cm
PC=390/210=1.86

PC values of 1.8 or less have previously been correlated to malignant degeneration of a tissue. PC values of 1.81 and higher have previously been correlated to chronic inflammation. Thus, in location 1, a diagnosis of malignant degeneration of the mucous (granulating gastric cancer) is made. In location 2, a diagnosis of chronic inflammation is made. Tissue biopsies taken from the same locations and analysed according to standard histopathological techniques confirm the diagnoses.

The apparatus and method of the invention allow one to objectively characterize the condition of the abdominal mucosa. The invention elevates the precision of morphologic diagnostics and alleviates the need to take 3–4 tissue biopsies. A single tissue biopsy is sufficient for an accurate diagnosis, thus reducing the cost of the procedure and trauma for the patient. In the case of a tumor, the invention allows the determination of the borders of the malignant growth, which is needed to properly select the operative intervention. The method of the invention is simple and does not require additional resources and services. Testing time is only 2–3 minutes. Studies carried out with the apparatus and method of the invention have shown a coincidence with the results of histology tests in 95.6% of 450 subjects.

EXAMPLE 3

Intraoperative Diagnosis of Thyroid Cancer.

Preoperational clinical and special radioisotope methods of diagnosis do not provide an analysis of morphostructural characteristics of formed thyroid tissue nodes. At the moment the determination of the pathology of the thyroid is derived during an operation. In addition, surgery produces an analysis of pathology visually and by palpation, both of which are deprived of objective measurement. Also, the instant morphological diagnosis produced during surgery is expensive and long term as to the time (30–40 minutes). Moreover, biopsies selected during surgery by visual observation do not reduce the errors in the results. Lastly, the process is complicated and it's implementation demands professional skills.

The essence of the new method of the invention for intraoperative diagnosis of thyroid cancer is in the impedance measurement of thyroid tissues and measurement of all nodes during the operation. It enables the following analysis: (1) A determination of the benign or malignant nature of the tissue growth process; (2) An identification of the biopsy location for histologic examination, which raises the efficiency of the early diagnosis of thyroid cancer from 80% to 93.3%; and (3) In the case of the determination of the presence of a tumour, the present invention allows one to determine the borders of the tumour and to choose the tactics of the operative cure.

The apparatus and method of the invention utilised in Example 1 was employed, without the bronchoscope. The apparatus of the invention was brought into contact with the thyroid during thyroid surgery. The time of testing is about 15 to about 30 seconds. The method is simple and does not require laboratory services. Tests were conducted in Russia with 190 patients with benign and malignant tumours of the thyroid. Test results are compared to a set of data correlating electrical resistanc e measurements with thyroid tissue status. Diagnosis with the apparatus and method of the present invention was coincident with diagnosis from histopathology studies in 93.3% of cases.

EXAMPLE 4
Detection of Acute Blood Loss.

One of the most popular methods for detecting acute blood loss in clinical practice is the radioisotope method. This method has several disadvantages, however. The method requires 1–1.5 hours and thus has limited application to emergency situations. The method requires special laboratory services and equipment. Lastly, the method exposes personnel and patients to some degree of danger due to the utilisation of a radioisotope. The method of the invention employing the apparatus of the invention, on the other hand, is very simple, fast, inexpensive, and can be carried out in any condition (e.g., in the clinic, on the highway, in remote locations and in military conditions) by one person. The apparatus and method of the invention allow one to determine not only the rate of blood loss, but also the alkaline reserve of blood, globular volume of blood, the scope of circulating plasma, total circulating protein, the volume of circulating erythrocytes and hematocrit number.

The apparatus and method of the invention for measuring acute blood loss is illustrated in the present example as follows: The apparatus and method of the invention utilised in Example 1 was employed, without the bronchoscope and without tissue sampling. The essence of the method is in the measurement of the electrical resistance of 1.0 ml of a patient's blood. The time required for testing is about 1–2 minutes. The aspirating needle 8 for sampling blood is used in the following manner: the protecting cap is removed from flange 10, and the syringe 11 by tip 12b is tightly inserted into flange 10. Piston 13 is initially in the input position (is maximally proximate to tip 12b). Blood is then aspirated in the syringe in a volume of about 1.0 milliliters in the conventional manner by withdrawing piston 13.

Resistance measurements on the blood sample are made in the following manner: clamp 20 is connected to the acting end of metal piston 13 and probe 21 is inserted into jack 18. In the "closed" electrical circuit the syringe 11 with metal piston 13 and tip 12b serves as a cell, in which the metal tip 12b serves as active electrode and piston 13—as passive electrode. In other words—syringe 11 with tip 12b provides reliable electrical contact with the flange 10, and lead 19, connected by clamp 20 with piston 13 and inserted in jack 18 by leg 21 allows the measurement of specific resistance in the volume of the syringe cell 11 (in the volume of 1.0 milliliters). All of the measurements of specific resistance of a blood sample in the syringe cell 11 are carried out similarly to measurements of specific resistance on biological tissue. Test results are compared to a set of data correlating electrical resistance measurements to acute blood loss and specific parameters such as globular volume of blood, scope of circulating plasma, total circulating protein, volume of circulating erythrocytes and hematocrit number.

EXAMPLE 5
Diagnosis and Forecasting of Lactation Mastitis.

The apparatus and method of the invention utilised in Example 4 was employed for the early instant diagnosis of lactational mastitis. The essence of the method is in the measurement of the electrical resistance of 0.5 ml of a female's milk. The time required for testing is about 15–30 seconds. Test results are compared to a set of data correlating electrical resistance measurements of milk to mastitis disease state. The results of the testing enable one to make the following observations and conclusions:

(1) The initial degree of development of the inflammatory process in the mammary gland can be monitored. The illness is detected in the very early stages of development—14 days before clinical signs of illness;

(2) One can differentiate lactostasis and mastitis;

(3) One can differentiate different forms of mastitis (seasonal, infiltrative, maternal), which simplifies the choice of tactics for cure;

(4) The course of the post-operative term during maternal mastitis can be forecasted; and (5) One can detect the degree of infectivity of the milk.

EXAMPLE 6
Differential Diagnosis of Fibroadenoma and Breast Cancer.

The apparatus and method of the invention enable the differential diagnosis of fibroadenoma and breast cancer. The apparatus and method of the invention utilised in Example 1 was employed, without the bronchoscope. A diagnosis is produced via the insertion of aciform electrodes in the mammary gland and measurements of its impedance at different frequencies. Test data are once again compared to a data set correlating electrical resistance measurements to tissue status. The method allows one to conduct a differential diagnosis between benign and malignant mastoncus with a reliability of 90% and to differentiate different morphologic forms of malign new growths (adenocarcinal carcinoma). The time required for a diagnosis is 1–2 minutes. Again, no additional laboratory equipment or specially trained personnel are required. Diagnosis with the apparatus and method of the present invention was coincident with diagnosis from histopathology studies in 89.7% of cases.

EXAMPLE 7
Diagnosis of Larynx Cancer.

The apparatus and method enable the diagnosis of larynx cancer. The apparatus and method of the invention utilized in Example 1 is employed, without the bronchoscope. The diagnosis is produced via the insertion of electrodes into the tissue of the larynx and measuring the electrical resistance at two different frequencies. Test data are compared with data on healthy larynx tissue. The method enables the differentiation of the various desease forms of the tissue in border states. The time required for diagnosis is 2–4 minutes.

EXAMPLE 8
Diagnosis of Thermal Injury of Soft Tissues.

The apparatus and method of the invention utilized in Example 1 was employed, without the bronchoscope. The diagnosis is produced via the insertion of the electrodes into the soft tissue to the depth depending on the amount of thermal injury and measuring of the electrical resistance of the tissue at two different frequencies. Test data are compared with data correlating electrical resistance measurements of soft tissue with soft tissue status, healthy or otherwise. The diagnosis with said apparatus and method of the present invention was coincident with histology diagnosis in 79.8% of cases.

What is claimed is:

1. An assembly kit for an apparatus for simultaneously obtaining a biological sample and measuring the electrical resistance of said sample at at least two different frequencies for diagnosis of a condition of said sample, comprising: a main case comprising a tube and demountable handle; an aspirating needle adapted to be connected to the main case at least partially inside said tube, for obtaining a sample of biological liquid and for serving as an active electrode in contact with said biological sample; a liquid collector adapted to be connected to said aspirating needle to receive said sample of said biological liquid, said liquid collector comprising a metal conductor in electrical contact with said needle and a metal piston, wherein at the determination of said condition of said biological liquid said needle executes the role of active electrode, and said metal piston executes the role of passive electrode; and an electroimpedancemeter adapted to be electrically connected to said active and passive electrodes, for simultaneous measurement of said electrical resistance of the sample at at least two different frequencies.

2. The assembly kit as defined in claim 1, further comprising a hook adapted to be attached to said tube, said hook comprising a pointed end for obtaining a sample of biological tissue, wherein at the determination of said condition of said biological tissue said needle executes the role of active electrode, and said hook executes the role of passive electrode.

3. The assembly kit as defined in claim 1, wherein the main case has an electrical plug adapted to be electrically connected to each of said active and passive electrodes when assembled, wherein said electroimpedancemeter is electrically connected to said active and passive electrodes through the electrical plug.

4. The assembly kit as defined in claim 1, wherein the electroimpedanemeter comprises a source of alternating current voltage consisting of two generators, one for a first frequency voltage and the other for a second frequency voltage, the second frequency is higher than the first frequency.

5. The assembly kit as defined in claim 4, wherein the first frequency is in the range from about 0.5 to about 10 kHz.

6. The assembly kit as defined in claim 5, wherein the first frequency is in the range from about 1 to about 5 kHz.

7. The assembly kit as defined in claim 6, wherein the first frequency is in the range from about 1 to about 3 kHz.

8. The assembly kit as defined in claim 4, wherein the second frequency is in the range from about 10 to about 1000 kHz.

9. The assembly kit as defined in claim 8, wherein the second frequency is in the range from about 20 to about 500 kHz.

10. The assembly kit as defined in claim 9, wherein the second frequency is in the range from about 50 to about 300 kHz.

11. A method of simultaneously obtaining a biological sample and measuring electrical impedance of the sample for the purpose of diagnosis of a condition of the sample comprising: contacting a biological tissue with an electrically conductive hook comprising a pointed end as a first electrode and a second electrode; measuring electrical impedance of the biological tissue contacted with the first and second electrodes at at least two different frequencies; and excising a part of the biological tissue with the pointed end of the hook to obtain a sample of the biological tissue.

12. The method as defined in claim 11, wherein the second electrode comprises an aspirating needle connected to a syringe, the method further comprising: inserting the aspirating needle into the biological tissue when contacting the biological tissue; withdrawing a sample of biological liquid retained in the biological tissue into the syringe through the aspirating needle; and measuring electrical impedance of the sampled biological liquid in the syringe at at least two different frequencies.

13. The method as defined in claim 11, wherein the electrical impedance of the biological tissue or liquid is measured at a first and a second frequency.

14. The method as defined in claim 13, wherein the first frequency is in the range from about 0.5 to about 10 kHz.

15. The method as defined in claim 14, wherein the first frequency is in the range from about 1 to about 5 kHz.

16. The method as defined in claim 15, wherein the first frequency is in the range from about 1 to about 3 kHz.

17. The method as defined in claim 13, wherein the second frequency is in the range from about 10 to about 1000 kHz.

18. The method as defined in claim 17, wherein the second frequency is in the range from about 20 to about 500 kHz.

19. The method as defined in claim 18, wherein the second frequency is in the range from about 50 to about 300 kHz.

* * * * *

UNITED STATES PATENT AND TRADEMARK OFFICE
CERTIFICATE OF CORRECTION

PATENT NO. : 6,859,049 B2
DATED : February 22, 2005
INVENTOR(S) : Khatchatrian et al.

It is certified that error appears in the above-identified patent and that said Letters Patent is hereby corrected as shown below:

Column 23,
Line 26, delete "electroimpedanemeter" and insert -- electroimpedancemeter --.

Column 24,
Line 27, delete "10 kIlz" and insert -- 10 kHz --.

Signed and Sealed this

Seventeenth Day of January, 2006

JON W. DUDAS
*Director of the United States Patent and Trademark Office*